United States Patent [19]

Geria

[11] Patent Number: 4,992,476

[45] Date of Patent: * Feb. 12, 1991

[54] SKIN CLEANSING AND MOISTURIZING COMPOSITION AND METHOD OF USING AND PREPARING SAME

[75] Inventor: Navin M. Geria, Warren, N.J.

[73] Assignee: Warner-Lambert Company, Morris Plains, N.J.

[*] Notice: The portion of the term of this patent subsequent to Feb. 12, 2008 has been disclaimed.

[21] Appl. No.: 176,907

[22] Filed: Apr. 4, 1988

[51] Int. Cl.$^5$ .................... A61K 9/107; A61K 47/00
[52] U.S. Cl. .................... 514/782; 424/522; 424/523; 424/554; 424/555; 424/195.1; 514/772; 514/783; 514/784; 514/785; 514/817; 514/844; 514/845; 514/846; 514/847; 514/848; 514/938; 514/939; 514/941; 514/943
[58] Field of Search .............. 424/107, 195.1; 514/817, 844, 845, 846, 847, 848

[56] References Cited

U.S. PATENT DOCUMENTS

| | | | |
|---|---|---|---|
| 4,014,995 | 3/1977 | Juliano | 514/783 |
| 4,155,870 | 5/1979 | Jorgensen | 252/131 |
| 4,165,385 | 8/1979 | Lefebvre | 514/847 |
| 4,248,861 | 2/1981 | Schutt | 424/92 |
| 4,256,664 | 3/1981 | Epstein | 564/177 |
| 4,294,823 | 10/1981 | Elliott | 424/78 |
| 4,355,028 | 10/1982 | Kligman | 514/164 |
| 4,368,187 | 1/1983 | Flom | 424/81 |
| 4,368,189 | 1/1983 | Mentlik | 424/81 |
| 4,380,549 | 4/1983 | Van Scott | 514/23 |
| 4,382,960 | 5/1983 | Flom | 514/770 |
| 4,386,067 | 5/1983 | Guillon | 424/522 |
| 4,389,418 | 6/1983 | Burton | 514/785 |
| 4,459,285 | 7/1984 | Grollier et al. | 514/844 |
| 4,478,853 | 10/1984 | Chaussee | 424/78 |
| 4,563,346 | 1/1986 | Deckner | 514/847 |
| 4,794,106 | 12/1988 | Takashima | 514/179 |

FOREIGN PATENT DOCUMENTS 0038310 2/1985 Japan .................... 514/844

OTHER PUBLICATIONS

*Cosmetics Science and Technology*, Second Edition, Balsam and Sagarin, Eds., Wiley-Interscience, New York, 1974, vol. 1, Chapters 1,2,3 and 5, vol. 3, Chapter 44.
*Harry's Cosmeticology*, Seventh Edition, Wilkinson and Moore, Eds., Chemical Publishing, New York, 1982, Chapters 4 and 6.

*Primary Examiner*—Douglas W. Robinson
*Assistant Examiner*—Jean C. Witz
*Attorney, Agent, or Firm*—Carl W. Battle; Charles A. Gaglia, Jr.

[57] ABSTRACT

A long lasting, esthetically pleasing skin cleansing and care moisturizing composition comprising
(1) an oil phase comprising oil from about 30% to about 80% and a non-ionic surface active agent having an HLB number of about 7 to about 12, wherein the non-ionic surface active agent is present in an amount of about 5% to about 9%;
(2) an aqueous phase comprising an aqueous thickening agent from about 0.05% to about 5% and water from about 15% to about 65% wherein the oil phase is added to the aqueous phase to form an emulsion has been developed,
(3) an effective amount of an abrasive to remove oily deposits, cosmetics and particulates from the skin surface.

The method of preparation of the composition and a method of treating skin with the composition are also disclosed.

34 Claims, No Drawings

SKIN CLEANSING AND MOISTURIZING COMPOSITION AND METHOD OF USING AND PREPARING SAME

BACKGROUND OF THE INVENTION

Skin care products and in particular skin cleansing products generally contain alcohol and/or detergents which when applied to the skin, will exacerbate a preexisting dry skin condition and possibly cause a dry skin condition where none previously existed.

Dry skin is caused by an inadequate moisture content in the stratum corneum. The stratum corneum is a multicellular membrane of flattened, metabolically active cells which forms the outer layer of skin. The membrane is dynamic, constantly renewing itself as surface cells are lost through desquamation but replaced at an equivalent rate from underlying epidermal cells. This process maintains an essentially constant number of cell and a constant thickness in the stratum corneum.

The stratum corneum's water content must remain not less than approximately 10% to maintain normal skin hydration. At this moisture level, keratin (the horny skin layer) softens and attains a plastic state. This moisture level occurs in normal skin when the environment is at about 60% relative humidity. In the normal indoor environment, moisture content of the stratum corneum is about 10 to 15%. At 95% relative humidity, the stratum corneum's moisture content increases to about 65%. At low temperature and relative humidity, the outer skin layer dries out, becomes less flexible and may crack when flexed thereby increasing the rate of moisture loss.

Dry skin is characterized by one or more of the following: roughness or flaking; loss of flexibility; fissures; hyperkeratosis; inflammation and pruritus. While dry skin can occur at any season, it is especially prevalent in the winter and commonly found on the forearms, back of the hands, fingers and lower legs. Other causes of dry skin include disease, prolonged detergent use, malnutrition, age and physical damage to the stratum corneum Water is the only true plasticizer for human stratum corneum. The optimum treatment for dry skin is to raise the stratum corneum's moisture level and to reestablish its integrity. Approaches to treating dry skin include lubricating the skin; moisturizing the skin; chemically softening the keratinous epidermal layer; treatment with anti-inflammatory medicinal compounds. A detailed discussion of the approaches for treating dry skin is contained in *Handbook of Nonprescription Drugs*, eighth edition, Copyright 1986, American Pharmaceutical Assoc., Washington, D.C., Chapter 30, pages 597 to 631, the entire contents of which are hereby incorporated by reference.

Moisture diffuses to the keratin layer about 50 to 100 times faster than it is lost from the skin surface. Human skin is an effective barrier against water loss. Physical damage increases transepidermal water loss.

One of the primary treatments of dry skin involves the use of occlusive agents. Occlusives are hydrophobic substances that promote water retention by forming a barrier on the skin that will prevent moisture loss. The most commonly used occlusive agents include petrolatum, lanolin, cocoa butter, mineral oil and silicones.

Occlusives alone are not considered sufficient treatment. Patients are generally directed to soak the effected area in water for 5 to 10 minutes and then immediately apply the occlusive agent. This treatment will hydrate and then trap moisture in the skin. It is also believed that occlusives reestablish the integrity of the stratum corneum. In addition, occlusion may increase the metabolic rate of the epidermis, thereby increasing production of materials that become part of the stratum corneum. Caution must be exercised to avoid excessive hydration and maceration.

The best occlusive agents are, by their very nature, oleaginous having a greasy texture and are difficult to spread. More esthetic oil-in-water emulsions are preferred modes for applying occlusive agents. They are less effective, however, and rely on the aid of other formulating agents to form a film on the skin after the product's water content has evaporated.

While much effort has been directed to providing a highly effective, esthetically pleasing product none have been completely successful. The traditional approach has been to apply the occlusive product and produce the coating film in one step. The net result is that good esthetics are achieved at the expense of good occlusive films. Current products and methods of use have not been able to provide both a highly occlusive film and good esthetics in one product and method of use.

The composition and method of the present invention are directed to skin cleansing compositions which remove oil and particulate matter from the surface of skin while adding moisture to dry skin and applying a thin, long lasting occlusive film that is both effective and esthetically pleasing. The essential property of the present skin treating composition is that it increases stratum corneum flexibility by adding and sealing in moisture with a long lasting esthetically pleasing occlusive film.

SUMMARY OF THE INVENTION

It has surprisingly been found that a moisturizing skin cleansing and care composition of the occlusive type that is long lasting and esthetically pleasing is prepared by forming an oil phase containing an oil and a dissolved surface active agent and an aqueous phase containing a dispersed thickening agent. Then admixing the two phases by slowly adding the oil phase to the aqueous phase with high shear mixing to form an oil-in-water emulsion then adding tiny particles and uniformly dispersing them in the emulsion and recovering the final product. The product of the invention has an oil content of about 30% to about 80%.

DETAILED DESCRIPTION

In particular, it has been found that a long lasting, esthetically pleasing moisturizing skin cleansing and care composition is produced comprising forming an oil phase by dissolving a surface active agent into an oil and heating the mixture, forming an aqueous phase by dispersing an aqueous thickening agent in water and heating the mixture, forming an emulsion by slowly adding the heated oil phase to the heated aqueous phase with high shear mixing while maintaining an elevated temperature wherein addition of the oil phase to the water phase is at a slow uniform rate such that a physically stable emulsion is formed, and recovering the skin care composition.

A physically stable emulsion will not separate into layers on standing. The oil phase is formed with sufficient heating to facilitate mixing and dissolving the surface active agent in the oil. The aqueous phase is formed with sufficient heating to facilitate mixing and dispersing the aqueous thickening agent. The emulsion is formed with sufficient heating to facilitate mixing and emulsion formation.

More particularly, it has been found that a long lasting, esthetically pleasing moisturizing skin cleansing and care composition is produced comprising forming an oil phase by dissolving a surface active agent into an oil and heating to about 60° C. to about 80° C., forming an aqueous phase by dispersing an aqueous thickening agent in water and heating to about 60° C. to about 80° C.,forming an emulsion by slowly adding the oil phase to the aqueous phase with high shear mixing while maintaining a temperature of about 60° C. to 80° C. wherein addition of the oil phase to the water phase is at a uniform rate over a period of at least about 10 minutes, preferably about 10 minutes to about 30 minutes; the tiny particles are added to the emulsion with continued mixing until they are uniformly dispersed; and recovering the skin care composition.

When an aqueous thickening agent is used which requires neutralization, the procedure must contain the following process step after formation of the emulsion and before recovery of the product; neutralizing the emulsion by adding with moderate mixing an effective amount of a neutralizing agent to the emulsion such that a pH of about 4.5 to about 8.2 is attained while maintaining a temperature of about 60° C. to about 80° C.

The skin care composition of the present invention comprises (1) an oil phase comprising oil from about 30% to about 80% and a non-ionic surface active agent having an HLB number of about 7 to about 12, wherein the non-ionic surface active agent is present in an amount of about 5% to about 9%; (2) an aqueous phase comprising an aqueous thickening agent from about 0.05% to about 5% and water from about 15% to about 65%, and (3) an effective amount of tiny polymer particles to aid skin cleansing, all percents are by weight of the final composition.

The method of treating and cleansing skin of the present invention comprises applying to said skin an effective amount of a skin care composition comprising (1) an oil phase comprising oil from about 30% to about 80% and a non-ionic surface active agent having an HLB number of about 7 to about 12, wherein the non-ionic surface active agent is present in an amount of about 5% to about 9%; (2) an aqueous phase comprising an aqueous thickening agent from about 0.05% to about 5% and water from about 15% to about 65% and (3) an effective amount of tiny particles to aid skin cleansing and washing the treated skin with water to remove excess skin care composition leaving the skin with a coating having smooth velvety feel, all percents are by weight of the skin care composition. The skin care composition may optionally contain a neutralizing agent.

The skin cleansing and care composition of the present invention provides an oil in water emulsion having high oil content from about 30% to about 80%. Compositions having such high oil content are generally physically unstable and "greasy" or "oily". The present inventive composition is physically stable. In addition, the present invention when applied to the skin produces an "oily" coating. Surprisingly the "oily" coating is readily washed off with water leaving the skin coated with a smooth "velvety", "non-oily" film of oil. The residual oil film is resistant to further washing and remains on the skin for about 8 hours.

While the invention is not to be limited to theoretical considerations, it is believed that incorporation of the thickening agent into the aqueous phase physically stabilizes the emulsion providing for a long shelf life and a pharmaceutically acceptable appearance. It is further believed, that incorporation of a non-ionic surface active agent having an HLB number between about 7 to about 12 provides the oil in water emulsion with special properties. Emulsions of the present invention are high in oil content yet water washable. In addition, these emulsions leave a long lasting velvety feeling layer of oil on the skin. The surfactant functions to aid emulsion formation and impart a water compatible property to the oil allowing an oil film to adhere to the skin surface after washing with water. The tiny particles act as an abrasive to physically break up and/or erode deposits and particulates on the skin surface.

The oil phase of the present invention comprises an oil and a non-ionic surface active agent. Oil acts as an occlusive agent. The oils useful in the present invention are varied and may be of animal, vegetable or mineral origin. Methods of producing oils are known and not a subject of the present invention. Animal oils are derived from the organs and tissues of animals and may be collected through extraction, heating and/or expressing processes. Vegetable oils are usually derived from the seeds of various plants and are generally produced by extraction or pressing processes. Mineral oils are derived from petroleum and are recovered through various refining processes. Throughout the specification and claims, the term "oil" shall be defined as any oil of animal, vegetable, synthetic or mineral origin in liquid form.

The oils useful in the present invention may be food grade edible oils or nonedible oils. For example, food grade oils would be particularly useful in edible pharmaceuticals and food products. Nonedible and edible oils would be useful in topical pharmaceuticals, cosmetics, personal care products and in lubricants.

Illustrative, nonlimiting examples of oils useful in the present invention include animal oils such as lanolin and the like, fatty acid esters and the marine oils; fish oil, whale oil, fish liver oil, seal oil, squalane and the like; vegetable oils such as castor oil, linseed oil, sunflower oil, soybean oil, olive oil, peanut oil, rapeseed oil, corn oil, safflower seed oil, cottonseed oil, coconut oil, palm oil, palm kernel oil, sweet almond oil, calophyllum oil, avacado oil, cerial germ oil, purcellin oil, and the like; mineral oils such as white mineral oil, parafin oil, petroleum jelly oil, petrolatum and the like. Synthetic oils such as silicone oils, dimethylpolysiloxane, cyclic silicones, methylphenylpolysiloxane, silicone-glycol copolymer and the like. Any of the oils may be used individually or in mixtures. The preferred oil is mineral oil.

Oil is present from about 30% to about 80%, preferably from about 55% to about 75% and most preferably from about 65% to about 75% by weight of the skin care composition. The preferred oil is mineral oil. Preferably, the mineral oil will have a viscosity of about 6.0 cps to about 85.0 cps.

An oil content of less than about 30% results in a composition that is too liquid, the emulsion being physically unstable. A composition with an oil content of more than about 80% does not form a stable emulsion.

A surface active agent, more commonly known as a surfactant, as used herein is an organic compound consisting of two parts: a hydrophobic portion, and a hydrophilic portion which renders the compound sufficiently soluble or dispersible in water or another polar solvent. The combined hydrophobic and hydrophilic portions render the compound surface-active and thus able to concentrate at the interface between a surface active agent oil solution and another phase such as an aqueous phase.

There are three types of surface active agents:
(A) non-ionic, which do not dissociate, but commonly derive their hydrophilic portion from polyhydroxy or polyethoxy structures; such as polyethylene oxides, polyoxyethylene fatty acid esters;
(B) anionic, where the hydrophilic portion of the molecule carries a negative charge: such as sodium lauryl sulfate, and linear alkyl sulfates, and
(C) cationic, where the hydrophilic portion of the molecule carries a positive charge: such as cetyl pryidinium chloride.

Non-ionic surface active agents are preferred in the present invention. Nonlimiting illustrative non-ionic surfactants include:

| Alkanolamides | |
|---|---|
| Fatty acid alkanolamides | $RCONHCH_2CH_2OH$ (ethanolamides) |
| Fatty acid dialkanolamides | $RCON(CH_2CH_2OH)_2$ |
| Polyethyleneglycol derivatives | |
| Alkyl polyglycol ethers | $R(OCH_2CH_2)_nOH$ |
| Alkyl aryl polyglycol ethers | $RC_6H_4(OCH_2CH_2)_nOH$ |
| Polyglycol esters | $RCO(OCH_2CH_2)_nOH$ |
| Thioethers | $RS(CH_2CH_2O)_nH$ |
| Polyethyleneimine derivatives | |
| Alkylpolyethyleneimine | $R(NHCH_2CH_2)_nNH_2$ |
| Polyethyleneimine amides | $RCONH(CH_2CH_2NH)_nH$ | wherein n is a whole number and R is a hydrophobic chain of about 12 to about 18 carbon atoms
Alkylated aryl polyether alcohol,
Polyethylene glycol tert-dodecyl thioether,
Fatty acid amide condensate,
Aromatic polyglycol ether condensate,
Secondary amide of lauric acid,
Fatty acid alkanomine condensate,
Sorbitan monolaurate,
Sorbitan monolauratepoloxyethylene derivative,
Sorbitan monooleate,
Sorbitan monooleate polyoxyethylene derivative, Another class of non-ionic surface active agents useful in this invention are ethoxylated hydrogenated castor oils. Such surfactants are prepared by hydrogenating castor oil and treating the so-formed product with from about 10 to 200 moles of ethylene glycol. They are designated as PEG (numeral) hydrogenated castor oil in accordance with the dictionary of the Cosmetics, Toiletries and Fragrance Association, 3rd Ed. wherein the numeral following PEG indicates the degree of ethoxylation, i.e. the number of moles of ethylene oxide added. Suitable PEG hydrogenated castor oils include PEG 16, 20, 25, 30, 40, 50, 60, 80, 100 and 200.

The preferred non-ionic surface active agents are polyoxyethylene fatty acid esters such as polyoxyethylene (2) stearyl ether (POE (2) stearyl ether), POE (2) oleyl ether, polypropylene glycol (5) ceteth 20 (PPG (5) ceteth 20), POE (50) stearate, POE (20) stearyl ether, and the like.

It is critical that the non-ionic surface active agent or mixture of non-ionic surface active agents have a hydrophilic—lipophilic balance number (HLB) of about 7 to about 12, preferably about 8 to about 11. The HLB is an important property of the non-ionic surface active agent since it determines the type of emulsion the surfactant tends to produce, i.e. oil in water or water in oil.

A surface active agent with an HLB number less than about 7 will not form an emulsion in the present system. While a surface active agent with an HLB number greater than about 12 will form a product that does not leave an oily fraction on the skin after working as the product will not bind to the skin.

A surface active agent that is lipophilic in character is assigned a low HLB number while a surface active agent that is hydrophilic is assigned a high number. A mixture of surface active agents will have an HLB number equivalent to a weighted average of the individual HLB numbers. For example, a surface active agent mixture of 1 part A, 2 parts B and 2 parts C, where the HLB number for A=5, B=15, and C=9 would be:

$$HLB_{mix} = 1/5 \times 5 + 2/5 \times 15 + 2/5 \times 9 = 9.6$$

The HLB value of non-ionic surface active agents are well known in the art. A typical list of HLB values for common surface active agents is found in *Cosmetics Science and Technology*, second edition, Vol.3, Balsam and Sagarin, Editors, Interscience Publishers, New York, 1974 pages 583 to 597, the entire contents of which are hereby incorporated by reference.

The surface active agent of the present invention may be single or a mixture. The amount of surface active agent in the present invention is about 5% to about 9%, preferable about 6% to about 8%. A surface active agent concentration greater than about 9% will produce a very hydrophilic composition which will not spread properly having a plastic flow instead of a thixotropic flow. Surface active agent content of less than about 5% will not hold an emulsion over time or at elevated temperatures and phase separation will occur. Freezing and thawing will also cause phase separation when the surface active agent content is less than about 5%.

The aqueous phase of the present invention comprises water and an aqueous thickening agent. Suitable thickening agents can comprise natural and synthetic gum, mixtures of gum, gelling agents and the like. Representative illustration include:
Natural gums: alginates, carrageenan, xanthan gum, gelatin, guar, gum arabic, carob, tragacanth, locust bean gum, karaya, pectin, agar, and
Synthetics: cellulose ethers and esters, methylcellulose, sodium carboxymethylcellulose, carboxymethylcellulose, hydroxypropylcellulose, carbomers and carbopol
Colloidal hydrated aluminum silicate: bentonite
Synthetic hectorite: laponite
Colloidal silica: aerosil and the like.

The aqueous thickening agent is present from about 0.05% to about 5% preferably about 0.1% to about 3% and most preferably about 0.1% to about 1%. When the thickening agent is present in an amount of less than about 0.05% the emulsion is physically unstable. At amounts greater than about 5% the aqueous phase will become too thick and an emulsion will not form. The thickening agents of the present invention may swell or gel on contact with water causing the viscosity to increase by adding structure to the aqueous phase. Alternatively, the thickening agent may be of the type requiring neutralization with a basic composition to cause increased structure and viscosity in the aqueous phase.

Examples of direct thickening agents include natural and synthetic gums, gels and cellulose derivatives. Typical thickening agents requiring neutralization include carbomers and carbopols.

When thickening agents requiring neutralizing agents are used, the neutralizing agent is added after the emulsion is formed with moderate stirring while maintaining a temperature of about 60 degrees C. to about 80 degrees C.

Mixing is continued until the emulsion is uniform generally about 5 to about 10 minutes.

Neutralizing agents useful in the present invention include aqueous soluble basic materials. Illustrative nonlimiting examples include basic alkali metal salts and alkaline earth metal salts such as hydroxides and carbonates and basic amine compounds such as triethanolamine, isopropylamine and the like. The ratio of thickening agent to neutralizing agent is about 1:4 to about 1:10. The pH of the emulsion after neutralization is about 4.5 to about 8.2.

Water is present in an amount of about 15% to about 65%, preferably from about 20% to about 40% and most preferably from about 25% to about 35%.

The tiny particles of the present invention act an an abrasive. The abrasives of the present invention may be selected from a wide range of compounds. The abrasives must be suitable for topical application and skin cleansing. Suitable tiny particles to act as an abrasive include but are not limited to pumice, cross-linked polystyrene, polymethylmethacrylate, polyethylene, aluminum oxide particles, polyester fibers and mixtures thereof.

The moisturizing and cleansing skin care composition will contain an effective amount of abrasive particles to remove oily deposits, cosmetics and particulates from the skin surface. Abrasives are present from about 2% to about 10%, preferably about 3% to about 5%. The shape of the abrasive particle is not critical, irregular, fiber, spherical, and semispherical or spheroidal shapes are all contemplated by the present invention.

The abrasive particulate size will vary greatly. In general, the abrasive particulate will have a particle size of about 3 to about 10 microns preferably about 5 to about 7 microns.

The present invention may further include ingredients such as colorants, preservatives, antioxidants, medicaments, moisturizers, sunscreen agents, germicides, deodorants, antiperspirants, healing agents, solvents, humectants, thickeners for the oily phase, emollients, buffers, fragrances, flavors and abrasives. These ingredients are generally added after the emulsion is formed.

The present invention is further illustrated by the following examples. All parts and percentages in the examples and throughout the specification and claims are by weight of the final composition unless otherwise indicated.

EXAMPLE 1

(Inventive Run A and Comparative Run 1)

This Example demonstrates the effect of rate of addition of the oil phase to the aqueous phase on formation of the skin care composition.

| Formula Ingredients | A (% w/w) | 1 (% w/w) |
| --- | --- | --- |
| Deionized Water | 20.15 | 20.15 |
| Methyl paraben | 0.20 | 0.20 |
| Propyl paraben | 0.10 | 0.10 |
| Imidazolidinyl Urea | 0.30 | 0.30 |
| Carbomer 940 | 0.15 | 0.15 |
| Triethanolamine 98% | 1.50 | 1.50 |
| POE (2) Stearyl Ether | 3.00 | 3.00 |
| Mineral Oil | 70.00 | 70.00 |
| PPG-5-ceteth-20 | 0.10 | 0.10 |
| POE (20) Stearyl Ether | 4.00 | 4.00 |
| Fragrance | 0.50 | 0.50 |
| TOTAL | 100.00 | 100.00 |
| HLB Number | 10.7 | 10.7 |

Procedure: the water was prepared by adding the methylparaben, propylparaben and imidazolidinyl urea (preservative) and carbomer 940 (thickener) to the water with mixing to disperse and then raising the water temperature to about 75 to 80 degrees C. with continued mixing.

The oil phase was prepared by adding the surface active agents PPG-5-CETETH-20, POE(2) stearyl ether and POE (20) stearyl ether to the oil with mixing then raising the temperature to about 75 to 80 degrees C.

The emulsion is then formed by adding the oil phase to the water phase and mixing at high shear.

In inventive Run A, the oil phase is added to the water phase at about 5 ml/minute equal to about 15 minutes. For comparative Run 1, the oil phase is added to the water phase at about 15 ml/minute equal to about 5 minutes.

The neutralizing agent is then added to the emulsion with mixing continuing until the product is uniform.

Run A forms a smooth creamy emulsion that is physically stable. The product is acceptable.

Run 1 forms a physically unstable product. Oil separates from the emulsion, the product deflocculates and is unacceptable.

EXAMPLE 2

(Comparative Runs 2 and 3)

This Example demonstrates the effect of surface active agents having an HLB number less than 7 and greater than 12. The compositions of this example are prepared by the process of Example 1 Run A. Run 2 has an HLB number of 16.2. Run 3 has an HLB number of 5.1.

| Formula Ingredients | 2 (% w/w) | 3 (% w/w) |
| --- | --- | --- |
| Deionized water | 20.15 | 20.15 |
| Methyl paraben | 0.20 | 0.20 |
| Proply paraben | 0.10 | 0.10 |
| Imidazolidinyl Urea | 0.30 | 0.30 |
| Carboxyvinyl Polymer 940 | 0.15 | 0.15 |
| Triethanolamine 98% | 1.50 | 1.50 |
| POE (2) Stearyl ether | 3.00 | — |
| POE (50) Stearate | — | 3.00 |
| Mineral Oil | 70.00 | 70.00 |
| PPG-5-ceteth-20 | 0.10 | 0.10 |
| POE (2) Oleylether | 4.00 | — |
| POE (20) Stearyl ether | — | 4.00 |
| Fragrance | 0.50 | 0.50 |
| Total | 100.00 | 100.00 |
| HLB Number | 16.2 | 5.1 |

Both Runs 2 and 3 produce products that are physically unstable. The oil separates out of the emulsion.

| Calculation of HLB | % of Total Surface Active Agent | HLB Number | Fractional HLB |
|---|---|---|---|
| Run 3 | | | |
| POE (2) Stearyl ether | 42.3 | 5.0 | 2.1 |
| POE (2) Oleyl ether | 56.3 | 4.9 | 2.8 |
| PPG (5) Ceteth 20 | 1.4 | 15.0 | 0.2 |
| Run 3 Total HLB Number | | | 5.1 |
| Run 2 | | | |
| POE (50) Stearate | 42.3 | 17.9 | 7.6 |
| POE (20) Stearyl ether | 56.3 | 15.0 | 8.4 |
| PPG (5) Ceteth 20 | 1.4 | 15.0 | 0.2 |
| Run 2 Total HLB Number | | | 16.2 |

EXAMPLE 3

(Inventive Runs B and C)

This Example demonstrates the effect of oil content on the emulsion. The compositions of this Example are prepared by the process of Example 1 Run A.

| Formula Ingredients | B % w/w | C % w/w |
|---|---|---|
| Deionized Water | 15.00 | 60.15 |
| Methyl paraben | 0.20 | 0.20 |
| Propyl paraben | 0.10 | 0.10 |
| Imidazolidinyl Urea | 0.30 | 0.30 |
| Carboxyvinyl Polymer 940 | 0.15 | 0.15 |
| Triethanolamine 98% | 1.50 | 1.50 |
| POE (2) Stearyl Ether | 3.00 | 3.00 |
| Mineral Oil | 75.15 | 30.00 |
| PPG-5-ceteth-20 | 0.10 | 0.10 |
| POE (20) Stearyl Ether | 4.00 | 4.00 |
| Fragrance | 0.50 | 0.50 |
| | 100.00 | 100.00 |
| HLB Number | 10.7 | 10.7 |

Run B product is stringy and pituitive, emulsion is acceptable but marginal.

Run C product is a thin liquid, emulsion is acceptable but marginal.

EXAMPLE 2

(Inventive Run D)

This Example demonstrates a skin cleansing and care composition of the present invention containing an abrasive particulate agent. The composition of this Example is prepared by the process of Example 1 Run A. The abrasive particulate was admixed into the emulsion until a uniform mixture was formed.

| Formula Ingredients | D (% w/w) |
|---|---|
| Polyethylene Particulate | 5.00 |
| Deionized Water | 16.55 |
| Methyl paraben | 0.20 |
| Propyl paraben | 0.10 |
| Imidazolidinyl Urea | 0.30 |
| Carbomer 940 | 0.15 |
| Sodium Hydroxide (10% w/w) | .10 |
| POE (2) Stearyl Ether | 3.00 |
| Mineral Oil | 70.00 |
| PPG-5-ceteth-20 | 0.10 |
| POE (20) Stearyl Ether | 4.00 |
| Fragrance | 0.50 |
| TOTAL | 100.00 |
| HLB Number | 10.7 |

The produce of Run D was found to remove cosmetic from human facial skin leaving the skin clean with a velvety smooth feel.

The invention being thus described, it will be obvious that the same may be varied in many ways. Such variations are not be regarded as a departure from the spirit of scope of the invention and all such modifications are intended to be included within the scope of the claims.

I claim:

1. A cleansing and moisturizing, occlusive skin care composition comprising, based on total weight of said composition:
   (1) an oil phase comprising oil selected from the group consisting of animal oils, vegetable oils, mineral oils, synthetic oils and mixtures thereof in an amount of from about 55% to about 75% and from about 5% to about 9% of a non-ionic surface active agent having an HLB number of about 7 to 12 and
   (2) an aqueous phase comprising an aqueous thickening agent selected from the group consisting of natural gums, synthetic gums, gelling agents and mixtures thereof in an amount of from about 0.05% to about 5% and water from about 20% to about 40%.
   and
   (3) an effective amount of an abrasive to remove oily deposits, cosmetics and particulates from skin surface, wherein said composition is prepared by
      (a) forming said oil phase by dissolving said non-ionic surface active agent into said oil and heating to about 60° C. to about 80° C. to facilitate solution;
      (b) forming said aqueous phase by dispersing said aqueous thickening agent in water and heating to about 60° C. to about 80° C. to facilitate dispersing; and
      (c) forming a stable oil-in-water emulsion by adding said oil phase to said aqueous phase with high shear mixing while maintaining said elevated temperature, wherein the addition of said oil phase to said aqueous phase is at a slow, uniform rate of at least about 10 minutes.

2. A method for preparing an occlusive cleansing and moisturizing skin care composition comprising, based on total weight of said composition:
   (a) forming an oil phase by dissolving about 5% to about 9% by weight of a non-ionic surface active agent having an HLB number of about 7 to about 12 into about 55% to about 75% by weight of an oil and heating to about 60° C. to about 80° C. to facilitate solution,
   (b) forming an aqueous phase by dispersing about 0.05% to about 5% by weight of an aqueous thickening agent in about 20% to about 40% by weight of water and heating to about 60° C. to about 80° C. to facilitate dispersing,
   (c) forming an emulsion by slowly adding said oil phase to said aqueous phase with high sheer mixing while maintaining said elevated temperature, wherein addition of said oil phase to said aqueous phase is at a slow uniform rate of at least about 10 minutes such that a stable oil-in-water emulsion is formed;

(d) admixing an effective amount of an abrasive to remove oily deposits, cosmetics and particulates from the skin surface, and (e) recovering said skin care composition.

3. The method of claim 2 further comprising the step of neutralizing said oil-in-water emulsion by adding an effective amount of a neutralizing agent.

4. The skin care composition of claim 1 wherein said aqueous phase further comprises an effective amount of a neutralizing agent.

5. A method of treating dry skin which comprises applying to the skin an effective amount of the cleansing and moisturizing skin care composition of claim 1 and
(B) washing the treated skin with water.

6. The composition of claims 1 or 4 wherein the oil is an animal oil selected from the group consisting of lanolin, fatty acid esters, fish oil, whale, oil, fish liver oil, seal oil, squalane and mixtures thereof.

7. The composition of claims 1 or 4 wherein the oil is a vegetable oil selected from the group consisting of castor oil, linseed oil, sunflower oil, soybean oil, olive oil, peanut oil, rapeseed oil, corn oil, safflower seed oil, cottonseed oil, coconut oil, palm oil, palm kernel oil, sweet almond oil, calophyllum oil, avacado oil, cerial germ oil, purcellin oil, and mixtures thereof.

8. The composition of claims 1 or 4 wherein the oil is a mineral oil selected from the group consisting of white mineral oil, parafin oil, petroleum jelly oil, petrolatum and mixtures thereof.

9. The composition of claims 1 or 4 wherein the oil is a synthetic oil selected from the group consisting of silicone oils, dimethylpolysiloxane, cyclic silicones, methylphenylpolysiloxane, silicone-glycol copolymer and mixtures thereof.

10. The composition of claims 1 or 4 wherein the non-ionic surface active agent is selected from the group consisting of alkanolamides, polyoxyethylenes, polyoxyethylene fatty acid esters, polyethyleneglycol derivatives, polyethyleneimine derivatives, ethoxylated hydrogenated castor oils.

11. The composition of claims 1 or 4 wherein the non-ionic surface active agent is selected from the group consisting of polyoxyethylene (2) stearyl ether, POE (2) oleyl ether, PPG (5) ceteth 20, POE (5) stearate, POE (20) stearyl ether and mixtures thereof.

12. The composition of claims 1 or 4 wherein the aqueous thickening agent is a natural gum selected from the group consisting of alginates, carrageenan, xanthan gum, gelatin, guar, gum arabic, carob, tragacanth, locust bean gum, karaya, pectin, agar, and mixtures thereof.

13. The composition of claims 1 or 4 wherein the aqueous thickening agent is a synthetic gum selected from the group consisting of cellulose ethers and esters, methylcellulose, sodium carboxymethylcellulose, carboxymethylcellulose, hydroxypropylcellulose, carbomers and carbopol and mixtures thereof.

14. The composition of claims 1 or 4 wherein the aqueous thickening agent is selected from the group consisting of colloidal hydrated aluminum silicate, bentonite, synthetic hectorite, laponite, colloidal silica and mixtures thereof.

15. The composition of claim 4 wherein the neutralizing is selected from the group consisting of basic alkali metal salts, basic alkaline earth metal salts, basic amine compounds and mixtures thereof.

16. The composition of claim 4 wherein the neutralizing agent is selected from the group consisting of alkali metal and alkaline earth metal hydroxides and carbonates, triethanol amine isopropylamine and mixtures thereof.

17. The method of claims 3 or 5 wherein the neutralizing agent is selected from the group consisting of basic alkali metal, basic alkaline earth metal salts, basic amine compounds and mixtures thereof.

18. The method of claims 3 or 5 wherein the neutralizing agent is selected from the group consisting of alkali metal and alkaline earth metal hydroxides and carbonates, triethanolamine, isopropylamine and mixtures thereof.

19. The method of claims 2, 3, or 5 wherein the oil is an animal oil selected from the group consisting of lanolin, fatty acid esters, fish oil, whale oil, fish liver oil, seal oil, squalane and mixtures thereof.

20. The method of claims 2, 3, or 5 wherein the oil is a vegetable oil selected from the group consisting of castor oil, linseed oil, sunflower oil, soybean oil, olive oil, peanut oil, rapeseed oil, corn oil, safflower seed oil, cottonseed oil, coconut oil, palm oil, palm kernel oil, sweet almond oil, calophyllum oil, avacado oil, cerial germ oil, purcellin oil, and mixtures thereof.

21. The method of claims 2, 3, or 5 wherein the oil is a mineral oil selected from the group consisting of white mineral oil, parafin oil, petroleum jelly oil, petrolatum and mixtures thereof.

22. The method of claims 2, 3, or 5 wherein the oil is a synthetic oil selected from the group consisting of silicone oils, dimethylpolysiloxane, cyclic silicones, methylphenylpolysiloxane, silicone-glycol copolymer and mixtures thereof.

23. The method of claims 2, 3, or 5 wherein the non-ionic surface active agent is selected from the group consisting of alkanolamides, polyoxyethylenes, polyoxyethylene fatty acid esters, polyethyleneglycol derivatives, polyethyleneimine derivatives ethoxylated hydrogenated castor oils.

24. The method of claims 2, 3, or 5 wherein the non-ionic surface active agent is selected from the group consisting of polyoxyethylene (2) stearyl ether, POE (2) oleyl ether, PPG (5) ceteth 20, POE (5) stearate, POE (20) stearyl ether and mixtures thereof.

25. The method of claims 2 or 3 wherein the aqueous thickening agent is a natural gum selected from the group consisting of natural gums, synthetic gums, gelling agents, mixtures thereof.

26. The method of claims 2, 3, or 5 wherein the aqueous thickening agent is a natural gum selected from the group consisting of alginates, carrageenan, xanthan gum, gelatin, guar, gum arabic, carob, tragacanth, locust bean gum, karaya, pectin, agar, and mixtures thereof.

27. The method of claims 2, 3, or 5 wherein the aqueous thickening agent is a synthetic gum selected from the group consisting of cellulose ethers and esters, methylcellulose, sodium carboxymethylcellulose, carboxymethylcellulose, hydroxypropylcellulose, carbomers and carbopol and mixtures thereof.

28. The method of claims 2, 3, or 5 wherein the aqueous thickening agent is selected from the group consisting of colloidal hydrated aluminum silicate, bentonite, synthetic hectorite, laponite colloidal silica and mixtures thereof.

29. The method of claim 3 wherein the neutralizing agent is selected from the group consisting of basic alkali metal salts, basic alkaline earth metal salts, basic amine compounds and mixtures thereof.

30. The method of claim 3 wherein the neutralizing agent is selected from the group consisting of alkali metal and alkaline earth metal hydroxides and carbonates, triethanol amine, isopropylamine and mixtures thereof.

31. The composition of claims 1 or 4 wherein the oil is mineral oil.

32. The method of claims 2, 3, or 5 wherein the oil is mineral oil.

33. The composition of claims 1 or 4 wherein the abrasive is selected from the group consisting of pumice, cross-linked polystyrene, polymethylmethacrylate, polyethylene, aluminum oxide particles, polyester fibers and mixtures thereof.

34. The composition of claims 2, 3, or 5 wherein the abrasive is selected from the group consisting of pumice, cross-linked polystyrene, polymethylmethacrylate, polyethylene, aluminum oxide particles, polyester fibers and mixtures thereof.

* * * * *